United States Patent
Wernimont et al.

(10) Patent No.: US 11,666,037 B2
(45) Date of Patent: Jun. 6, 2023

(54) SYSTEM AND METHOD FOR ASSOCIATING ANIMAL BEHAVIORS WITH ANIMAL HEALTH

(71) Applicants: Hill's Pet Nutrition, Inc., Topeka, KS (US); Georgia Tech Research Corporation, Atlanta, GA (US)

(72) Inventors: Sue Wernimont, Lawrence, KS (US); Kathy Gross, Topeka, KS (US); Rob Thompson, Newcastle upon Tyne. (GB); Jason Zutty, Atlanta, GA (US)

(73) Assignees: Hills Pet Nutrition, Inc., Topeka, KS (US); Georgia Tech Research Corporation, Atlanta, GA (US)

( * ) Notice: Subject to any disclaimer, the term of this patent is extended or adjusted under 35 U.S.C. 154(b) by 397 days.

(21) Appl. No.: 16/718,629

(22) Filed: Dec. 18, 2019

(65) Prior Publication Data

US 2020/0205381 A1 Jul. 2, 2020

Related U.S. Application Data

(60) Provisional application No. 62/892,317, filed on Aug. 27, 2019, provisional application No. 62/785,268, filed on Dec. 27, 2018.

(51) Int. Cl.
*A01K 29/00* (2006.01)
*G16H 50/30* (2018.01)
(Continued)

(52) U.S. Cl.
CPC .......... *A01K 29/005* (2013.01); *A61B 5/1116* (2013.01); *A61B 5/742* (2013.01);
(Continued)

(58) Field of Classification Search
None
See application file for complete search history.

(56) References Cited

U.S. PATENT DOCUMENTS

| 8,437,980 B2 | 5/2013 | Yuen et al. |
| 8,683,952 B2 | 4/2014 | Miller |

(Continued)

FOREIGN PATENT DOCUMENTS

| CN | 105705009 | 6/2016 |
| CN | 109068983 | 12/2018 |

(Continued)

OTHER PUBLICATIONS

Krieger, Stefanie, et al. "Prediction of calving in dairy cows using a tail-mounted tri-axial accelerometer: A pilot study." Biosystems Engineering 173 (2018): 79-84. (Year: 2018).*

(Continued)

*Primary Examiner* — Benjamin S Melhus

(57) ABSTRACT

A system, apparatus, and/or method of determining a health condition of an animal is provided. First data may be received from a first sensor device. The first data may be indicative of an animal event of an animal. Second data may be received from a second sensor device. The second sensor may be separate and/or distinct from the first sensor device. The second data may confirm an occurrence of the animal event. The animal event may be a discharge event and/or a feeding event. The occurrence of the animal event may be identified based on the first data and the second data. The occurrence of the animal event may be displayed via a display device. A health condition of the animal may be determined based on the animal event. The determination of the health condition may be based on a quantity and/or a duration of the animal event.

6 Claims, 8 Drawing Sheets

(51) Int. Cl.
G06F 3/01 (2006.01)
A61B 5/11 (2006.01)
A61B 5/00 (2006.01)

(52) U.S. Cl.
CPC ............ *G06F 3/017* (2013.01); *G16H 50/30* (2018.01); *A01K 2227/10* (2013.01); *A61B 2562/0219* (2013.01)

(56) References Cited

U.S. PATENT DOCUMENTS

| | | | |
|---|---|---|---|
| 8,704,668 | B1 | 4/2014 | Hagstrom |
| 8,797,166 | B2 | 8/2014 | Triener |
| 9,510,566 | B2 | 12/2016 | Pantazes |
| 9,770,013 | B2 | 9/2017 | Kim et al. |
| 10,149,617 | B2 | 12/2018 | Couse |
| 10,517,275 | B2 | 12/2019 | Harty et al. |
| 2005/0161007 | A1 | 7/2005 | Sunstrum |
| 2010/0302004 | A1 | 12/2010 | Winstead et al. |
| 2012/0299731 | A1* | 11/2012 | Triener ............ A01K 7/00 702/19 |
| 2013/0014706 | A1* | 1/2013 | Menkes ........... A61B 5/0004 119/859 |
| 2014/0331942 | A1 | 11/2014 | Sarazyn |
| 2015/0039239 | A1* | 2/2015 | Shuler ............ G16H 40/67 702/19 |
| 2016/0012748 | A1* | 1/2016 | Donavon ........... G09B 5/02 434/225 |
| 2016/0198960 | A1* | 7/2016 | Menkes ........... A61B 5/02055 119/859 |
| 2016/0262356 | A1 | 9/2016 | Perez-Camargo et al. |
| 2016/0310012 | A1 | 10/2016 | Mankowski |
| 2017/0000090 | A1* | 1/2017 | Hall .............. A01K 29/005 |
| 2017/0272843 | A1* | 9/2017 | Dror .............. A61B 5/0002 |
| 2019/0029226 | A1* | 1/2019 | Triener ........... G01G 17/08 |
| 2020/0345271 | A1* | 11/2020 | Filipowicz ........ A61D 17/00 |

FOREIGN PATENT DOCUMENTS

| | | | |
|---|---|---|---|
| DE | 102014108443 | | 12/2015 |
| EP | 3168821 | | 5/2017 |
| JP | 2006-042670 | | 2/2006 |
| JP | 2010-517565 | | 5/2010 |
| JP | 2014223060 | | 12/2014 |
| JP | 2016-514961 | | 5/2016 |
| JP | 2017-068856 | | 4/2017 |
| JP | 2017-527264 | | 9/2017 |
| JP | 2018-517400 | | 7/2018 |
| KR | 20180013230 | | 2/2018 |
| KR | 20190025160 | A * | 3/2019 |
| WO | 2015/107521 | | 7/2015 |
| WO | WO-2016023716 | A1 * | 2/2016 ............ A01K 1/01 |
| WO | 2016/147085 | | 9/2016 |
| WO | 2017/125805 | | 7/2017 |

OTHER PUBLICATIONS

KR20190025160A Machine Translation (Year: 2019).*
Aguirre et al., 2016, "Implementation and Analysis of a Wireless Sensor Network-Based Pet Location Monitoring System for Domestic Scenarios," Sensors 16(9):1384.
Clark et al., 2014, "Evaluation of a novel accelerometer for kinetic gait analysis in dogs," Canadian Journal of Veterinary Research 78(3):226-232.
Dicerbo et al., 2017, "Behavioral Disturbances: An Innovative Approach to Monitor the Modulatory Effects of a Nutraceutical Diet," Journal of Visualized Experiments 119:e54878.
Fitbark, "Meet the smallest, lightest dog GPS & health trackers," www.fitbark.com [accessed from internet Jan. 30, 2020].
Garmin, 1996, "Garmin International" www.garmin.com [accessed from internet Jan. 30, 2020].
Gerencser et al., 2013, "Identification of behaviour in freely moving dogs (Canis familiaris) using inertial sensors," PLoS One 8(10):e77814.
GOPRO, 2019, "GoPro Fetch," www.gopro.com [accessed from internet Jan. 30, 2020].
Gruen et al., 2015, "Criterion Validation Testing of Clinical Metrology Instruments for Measuring Degenerative Joint Disease Associated Mobility Impairment in Cats," PLoS One 10(7):e0131839.
Guillot et al., 2013, "Characterization of osteoarthritis in cats and meloxicam efficacy using objective chronic pain evaluation tools," The Veterinary Journal 196(3):360-367.
Jones et al., 2014, "Use of accelerometers to measure stress levels in shelter dogs," Journal of Applied Animal Welfare Science 17(1):18-28.
Judah et al., 2017, "The development and validation of a Real Time Location System to reliably monitor everyday activities in natural contexts," PLoS One 12(2):e0171610.
Ladha et al., 2017, "GaitKeeper: A System for Measuring Canine Gait," Sensors (Basel) 17(2):309.
Lascelles et al., 2007, "Evaluation of client-specific outcome measures and activity monitoring to measure pain relief in cats with osteoarthritis," Journal of Veterinary Internal Medicine 21(3):410-416.
Link AKC Smart Collar GPS Dog Collar Smart Collars for Dogs—https://www.linkakc.com/ [accessed from internet Dec. 18, 2019].
Petpace, "Smart Dog Collar. Your dog can't alert you when something's wrong. PetPace can," www.petpace.com [accessed from internet Jan. 30, 2020].
Philips, 2004, "Actical for the scientific professional," http://www.actigraphy.com/solutions/actical [accessed from internet Jan. 30, 2020].
Pitpat, 2019, "Get the UK's favourite dog activity monitor," www.pitpat.com [accessed from internet Jan. 30, 2020].
Scollar, 2017, "The first modular smart collar for pets," www.scollar.com [accessed from internet Jan. 30, 2020].
Tabcat, 2020, "Find and protect your cat easily with Tabcat Cat Tracker," www.tabcat.com [accessed from internet Jan. 30, 2020].
Vetrax, "Advanced Behavior Monitoring," www.vetrax.com [accessed from internet Jan. 30, 2020].
Whistle Go & Go Explore GPS Pet Trackers, website https://www.whistle.com/ [accessed from internet Dec. 18, 2019].
Yashari et al., 2015, "Evaluation of a novel canine activity monitor for at-home physical activity analysis," BMC Veterinary Research 11:146.
Yonezawa et al., 2009, "Cat@Log: sensing device attachable to pet cats for supporting human-pet interaction," in Proceedings of the International Conference on Advances in Computer Entertainment Technology, ACM: Athens, Greece pp. 149-156.
International Search Report and Written Opinion of the International Searching Authority in International Application No. PCT/US2019/067065, dated Mar. 17, 2020.

* cited by examiner

SYSTEM AND METHOD FOR ASSOCIATING ANIMAL BEHAVIORS WITH ANIMAL HEALTH

CROSS-REFERENCE TO RELATED APPLICATIONS

This application claims the benefit of U.S. Provisional Patent Application No. 62/785,268, filed on Dec. 27, 2018, and U.S. Provisional Patent Application No. 62/892,317, filed on Aug. 27, 2019. The disclosures of the above applications are incorporated herein by reference.

BACKGROUND

When a pet or other animal becomes ill or injured, the animal is typically unable to communicate its symptoms or their cause. Although the animal can be taken to a veterinarian for a check-up, such visits are often expensive and inconvenient, and the veterinarian may not have enough information to accurately diagnose the animal. Delayed treatment of the underlying issue may result in pain or even death to the animal.

One can manually observe the animal to determine if the animal is injured or otherwise unhealthy. However, manual approaches are often cumbersome and do not provide a timely diagnosis of the animal's health condition. Further, manual observation of animals is prone to inaccuracies, incompleteness, and forgetfulness.

BRIEF SUMMARY

A system, apparatus, and/or method of determining a health condition of an animal is provided. First data may be received from a first sensor device. The first data may be indicative of an animal event of an animal. Second data may be received from a second sensor device. The second sensor may be separate and/or distinct from the first sensor device. The second data may confirm an occurrence of the animal event. The animal event may be a discharge event and/or a feeding event. The occurrence of the animal event may be identified based on the first data and the second data. The occurrence of the animal event may be displayed via a display device. A health condition of the animal may be determined based on the animal event. The determination of the health condition may be based on a quantity and/or a duration of the animal event.

In an aspect, a system, apparatus, and/or method for determining an animal health condition may be described. Data comprising first data and second data may be received. It may be determined that the first data is indicative of a first motion or orientation based on a comparison with first stored data. It may be determined that the second data is indicative of a second motion or orientation based on a comparison to second stored data. The second data may be distinct from the first data. An animal event may be determined based on the first motion or orientation and the second motion or orientation. The occurrence of the animal event may be displayed via a display device. A health condition of the animal may be determined based on the animal event. The determination of the health condition may be based on a quantity and/or a duration of the animal event.

BRIEF DESCRIPTION OF THE DRAWINGS

The present invention will become more fully understood from the detailed description and the accompanying drawings, wherein.

DETAILED DESCRIPTION

Figure 1:
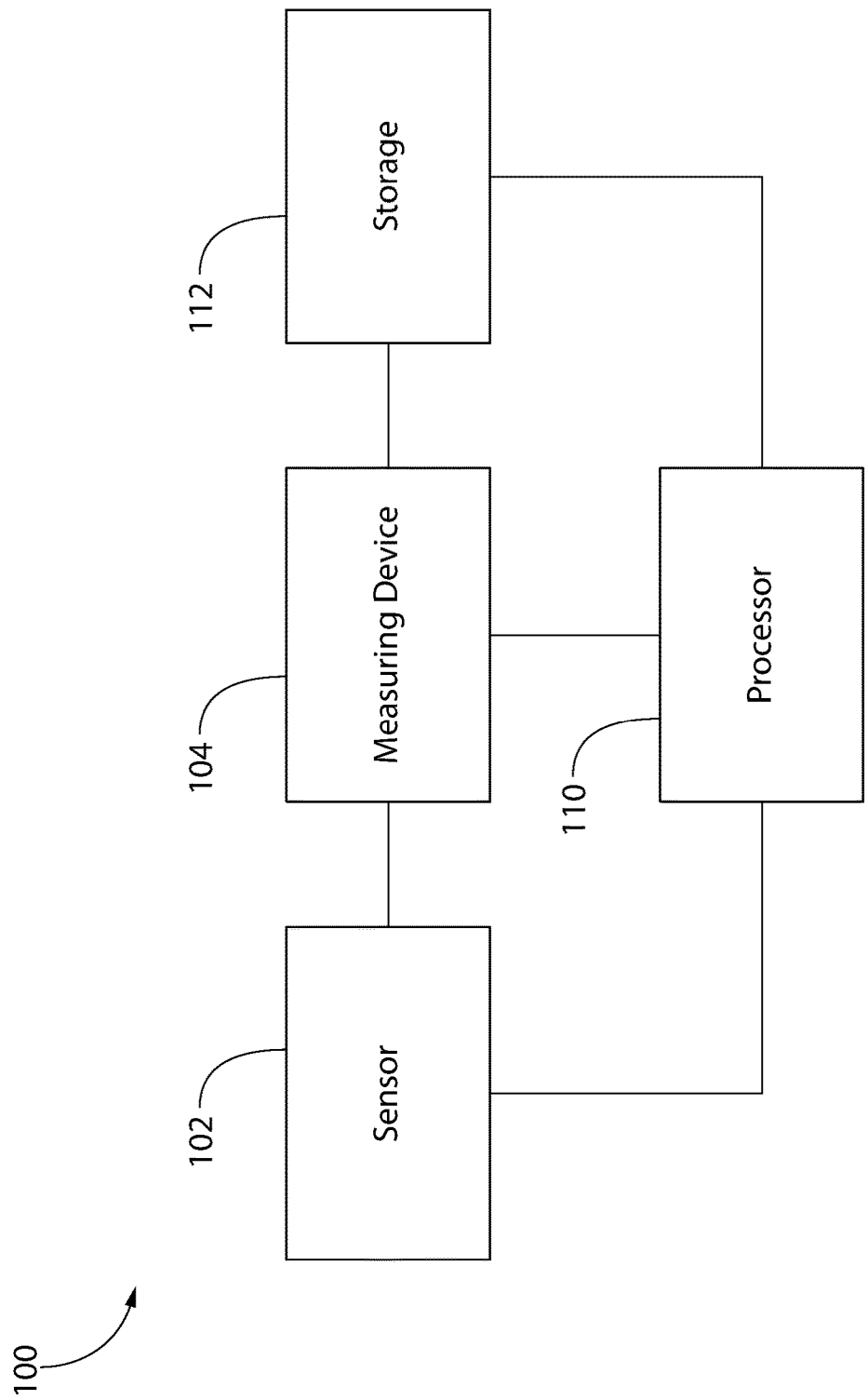
FIG. 1 is a block diagram of a system having a plurality of modules configured to collect and analyze the behavior of an animal.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top," and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

The system, method, and apparatus seek to provide health monitoring of an animal, for example, to determine a health condition of the animal. Example animals may be a pet (e.g., cat, dog, bunny, guinea pig, bird), a farm animal (e.g., a horse, cow, chicken), a zoo animal (e.g., a lion, bear), an animal in the wild, and the like. The health monitoring of the animal may provide (e.g., automatically provide) an early detection of an animal's health abnormality (e.g., sickness, disease, injury, etc.). Early detection of the animal's health abnormality may result in many benefits to the animal, especially if the animal's caretaker or an animal doctor takes corrective action as result of the detected health abnormality. The system may be designed for use at the home of the animal and may lead to vital information being provided to the animal's care taker and/or animal doctors. The system may include an activity collar, a waste area (e.g., a litter box), a food dish, a water bowl, or the like. A recognition device (e.g., on the activity collar worn by the animal) may identify the animal within the system. The animal may be linked to an animal profile.

The animal's behavior and/or habits may be monitored, tracked, and/or electronically recorded (e.g., automatically monitored, tracked, and/or electronically recorded) on a predefined frequency (e.g., on a daily, weekly, monthly, yearly basis). The animal's behavior may be used to determine the animal's health condition. The animal's behavior and/or habits may be monitored, tracked, and/or recorded without disturbing the animal or disrupting its natural behavior. For example, because animals come to their feeding area or waste area on their own terms, and on their own schedule, the behaviors and/or habits of the animal at the feeding area and/or waste area may be used to determine the animal's health condition.

While in the waste area, for example, the animal may freely move around and may perform activities such as sniffing, digging, crouching, and the like. The animal may move about the waste area to locate a spot to evacuate its bowels or bladder. During the bowel or bladder evacuation, the animal may focus on its action and may stop moving inside the waste area. The time before/after the animal evacuates its bowels or bladder, or the time during which the animal evacuates its bowel or bladder, may be distinguished based on the animal's movement or lack of movement.

In an example, the monitoring of the animal's health condition may be performed via collection of one or more types of data. The data may include motion data, location data, orientation data, spatial data, weight data, and the like. The data may be collected and/or monitored during one or more pet activities, such as eating, drinking, resting, urinating, and/or defecating. Collected data may be stored in a repository that is accessible to animal caregivers, veterinarians, and the like. The data may be accessible via a portable electronic device (e.g., an application of a portable electronic device) and/or a server. A portable electronic device may be one or more of a number of devices, including without limitation, a smart phone, a cell phone, a tablet computer, a personal digital assistant ("PDA"), a laptop computer, etc. The data may be analyzed to identity behavior and/or habits of the animal, and to provide the data and/or advice to owners based on the data. The data may be collected and/or generated over time, for example, for statistical processing of the animal's behaviors and/or habits. The data may be compared with previously collected and/or stored data for purposes of understanding the animal's health trends, variations in an animal's state of health, for determining whether a health abnormality exists for the animal, etc. The previously collected and/or stored data may relate to the animal that is being monitored and/or the previously collected and/or stored data may relate to another animal (e.g., for comparison purposes).

As described herein, an animal's actions with respect to eating, drinking, urinating, defecating, and/or resting may be monitoring for determining if the animal has a health abnormality. An animal being treated (e.g., by the caregiver or an animal doctor) for a health abnormality may be observed and/or monitored to determine if the treatment is improving the animal's condition. The health parameters monitored and stored over time (e.g., as historical data) may be used by an animal doctor and/or the caretaker to assess trends and changes in the animal's state of health over time.

An animal's health condition, such as whether the animal is suffering from an injury, an illness, a disease, etc., may be determined and/or recorded. To determine the animal's health condition, parameters indicative of the animal's health condition may be monitored and/or recorded. Such parameters may include the amount of times the animal eats, drinks, sleeps, urinates, defecates in a time period, the duration of the eating, sleeping, urination, defecation, etc. As an example, the time period may be an hour, a day, a week, a month, or the like.

Application of statistical methods may be used to derive information about the animal's health condition. For example, a healthy animal may be expected to drink, eat, sleep, urinate, and/or defecate a minimum and/or maximum amount of times during a time period. A mean and median of the above parameters may be defined for a healthy animal and/or for an unhealthy animal. If the animal performs a defined health parameter less than or more than an amount defined for a healthy animal, the animal may be identified as being unhealthy (e.g., a sick, injured, diseased, etc.). Subsets of characteristics of the animal may be used to determine whether an animal's behaviors and/or habits are indicative of a healthy animal or an unhealthy animal. Such characteristics may include the specie, bread, age, gender, geographic location, size/weight, of the animal.

Parameters determined, identified, received, and/or transmitted may be recorded. The parameters may be recorded continuously, for example, from the moment of system activation throughout animal's life. In other examples, the parameters may be recorded for a predefined time period (e.g., for a day, a week, a month, etc.), on a predefined frequency (e.g., every weekday), etc.

FIG. 1 shows an example system for monitoring an animal's behavior, health, habits, and/or other characteristics. System 100 may include a sensor 102, a measuring device 104, and/or a storage device 112.

Sensor 102 may be configured to detect a location of the animal, to detect the motion (or stillness) of the animal, to detect an orientation of the animal, etc. Sensor 102 may be one or more of a variety of form factors, including, but not limited to, an accelerometer, a gyroscope, a magnetometer, weighing scales, weight transducers, force transducers, displacement transducers, pressure transducers, weight sensors, force sensors, displacement sensors, pressure sensors, load cells, photographic cameras, video cameras, camcorders, contact thermometers, non-contact thermometers, and a combination thereof. In addition, or alternatively, sensor 102 may be one or more of optical sensors, optical reflecting sensors, LED/photodiode pair optical sensors, LED/phototransistor pair optical sensors, laser diode/photodiode pair optical sensors, laser diode/phototransistor pair optical sensors, optocouplers, optical fiber coupled optical sensors, magnetic sensors, weight sensors, force sensors, displacement sensors, pressure sensors, various proximity sensors, such as inductive proximity sensors, magnetic proximity sensors, capacitive proximity sensors, and/or a combination thereof. Sensor 102 may include communication circuitry, such as blue tooth, RFID, Wi-Fi and other wireless technologies. Sensor 102 may communicate with one or more devices, for example, sensor 102 may communicate with a server.

Measuring device 104 may be configured to measure a characteristic related to the animal. Measuring device 104 may be implemented in one or more of a variety of form factors, including, but not limited to, weighing scales, weight transducers, force transducers, displacement transducers, pressure transducers, weight sensors, force sensors, displacement sensors, pressure sensors, real time clocks, timers, counters, and/or a combination thereof. Measuring device 104 may include communication circuitry, such as blue tooth, RFID, Wi-Fi and other wireless technologies. Measuring device 104 may communicate with one or more devices, for example, measuring device 104 may communicate with a server.

Storage device 112 is may be configured to store data provided to and/or from system 100. The data may include motion data and/or location data provided by the sensor 102, for example. Example storage devices 112 may be memory devices, data storage devices, and a combination thereof, such as memory chips, semiconductor memories, Integrated Circuits (IC's), non-volatile memories or storage device such as flash memories, Read Only Memories (ROM's), Erasable Read Only Memories (EROM's), Electrically Erasable Read Only Memories (EEROM's), Erasable Programmable Read Only Memories (EPROM's), Electrically Erasable Programmable Read Only Memories (EEPROM's), an Electrically Erasable Programmable Read Only Memory (EEPRO), volatile memories such as Random Access Memories (RAM's), Static Random Access Memories (SRAM's), Dynamic Random Access Memories (DRAM's), Single Data Rate memories (SDR's), Dual Data Rata memories (DDR's), Quad Data Rate memories (QDR's), microprocessor registers, microcontroller registers, CPU registers, controller registers, magnetic storage devices such as magnetic disks, magnetic hard disks, magnetic tapes, optical memory devices such as optical disks, compact disks (CD's), Digital Versatile Disks (DVD's), Blu-ray Disks, Magneto Optical Disks (MO Disks) and/or a combination thereof. In one embodiment, the storage device comprises a semiconductor RAM IC for an intermediate recording of the behavior, health, and/or characteristics of the animal, and then transfer of the data to a flash memory IC for non-volatile recording. Storage 112 may be an external memory device, such as a USB flash memory, an external hard drive, etc.

System 100 may include a processor 110 configured to calculate and/or process data provided to system 100, for example. Example processors may be electronic circuits, systems, modules, subsystems, sub modules, devices and combinations thereof, such as Central Processing Units (CPU's), microprocessors, microcontrollers, processing units, control units, tangible media for recording and/or a combination thereof. Storage device 112 may be configured to store derived data from the processor 110. Processor 110 may include communication circuitry, such as blue tooth, RFID, Wi-Fi and other wireless technologies. Processor 110 may communicate with one or more devices, for example, processor 110 may communicate with a server.

In an example, sensor 102, measuring device 104, and/or storage 112 may be assembled in a number of configurations, including in a stand-alone apparatus. In another example, sensor 102, storage 112, and processor 110 may be assembled in a stand-alone apparatus. In other examples, the processor 110 and/or storage 112 may be configured as remote devices, such as remote servers (e.g., cloud storage devices). Although FIG. 1 shows a connection between processor 110 and each of sensor 102, measuring device 104, and storage 112, examples should not be so limited. In examples one or more of the devices may communicate with one or more (including any, or none) of the other devices. For example, sensor 102 may communicate with processor 110 and storage 112, sensor 102 may not communicate with measuring device 104, etc. One or more devices may be added and/or removed from system 100. For example, additional sensors 102 may be added to system 100 and/or measuring device 104 may be removed from system 100.

Data relating to the animal may be processed and/or recorded for a determination of the animal's health condition. For example, the amount of times, durations, etc., that an animal eats, drinks, urinates, defecates, and/or rests may be used to determine a health condition of an animal. A weight of an animal, a weight of a waste deposited by an animal (e.g., in a waste area), a body temperature of an animal, a weight of the food and/or liquid consumed by the animal, the date of an event (e.g., an eating, drinking, defecating, urinating), the time of an event (e.g., an eating, drinking, defecating, urinating), and/or the time of a movement of the animal may be used to determine a health condition of an animal. The animal's use of a clothing, apparatus, etc., may be used to determine a health condition of an animal. For example, the animal's wearing of a bootie, use of an enclosure (e.g., joint enclosure, such as a knee/elbow enclosure), a harness, etc. may be used to determine a health condition of the animal. One or more activities of the animal may be recorded via a video recording, picture, and/or audio recording and/or may be processed.

Figure 2:
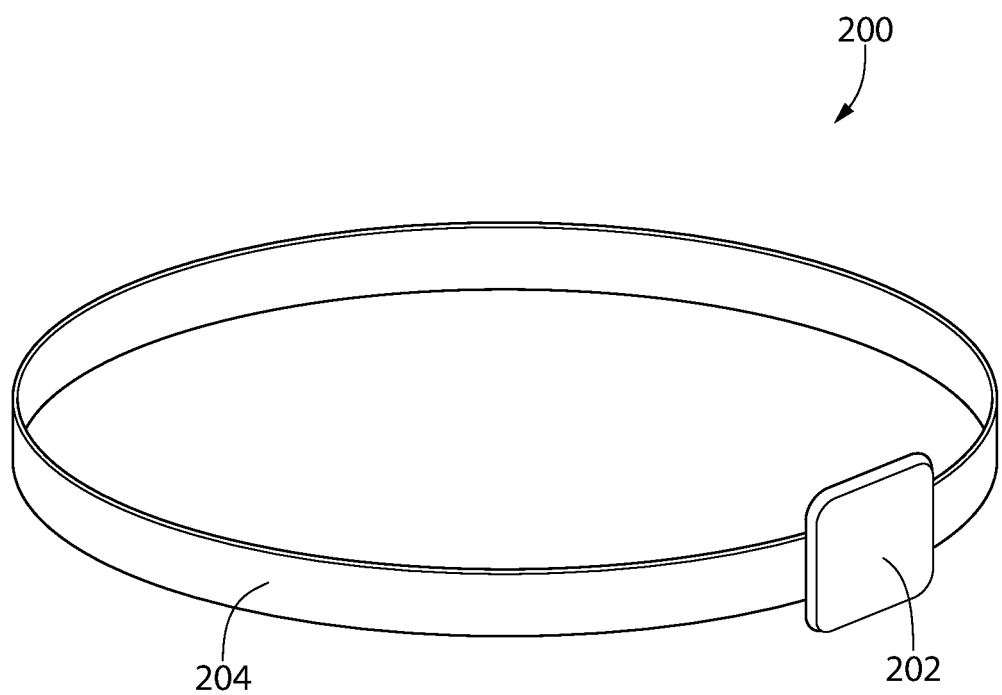
FIG. 2 is a perspective view of an example activity collar.

FIG. 2 is a perspective view of an example activity collar 200. Activity collar 200 may be linked to a particular animal (e.g., may be linked to a profile of a particular animal). Activity collar 200 may include circuitry 402 that is added to a collar portion 404. The circuitry 402 may include a processor, storage, wireless communication hardware, one or more sensors (e.g., accelerometers, gyroscopes, magnetometers, etc.), GPS, temperature sensors, moisture detectors, biometric sensors, etc. The wireless communication hardware may include a transmitter and a receiver. For example, the wireless communication hardware of the activity collar 200 may include a low energy communication device, such as Bluetooth Low Energy or RFID. The activity collar 200 may include a memory for storing data.

An accelerometer located on the activity collar 200 may be configured to measure motions of the animal. For example, the accelerometer may measure accelerations of the animal, changes in velocity of the animal, and/or changes in position of the animal. A gyroscope may be configured to measure changes in orientation of the animal and/or changes in rotational velocity of the animal. A magnetometer may be configured to measure orientation (e.g., absolute orientation) of the animal, for example, in the NESW plane.

As described above, the activity collar 200 may include a GPS. The GPS may track a position of the animal. For example, the GPS may indicate that the animal is within the waste area. When the animal enters the waste area, for example, automated alerts may be sent to the system to perform monitoring (e.g., monitoring of motion, orientation, and the like) of the animal via one or more sensors (e.g., accelerometer, gyroscope, proximity sensor, etc.). To save on battery life of the activity collar, for example, one or more of the devices within the activity collar may activate (e.g., only activate) when the animal crosses the perimeter. One or more sensors within the activity collar may only activate when the animal is within a waste area, about a waste area, and/or within a feeding area.

Activity collar 200 may send data relating to an animal to a server, feeding bowl, water dish, and/or litter box. For example, activity collar 200 may send motion data, orientation data, location data, etc., to a server, feeding bowl, water dish, and/or litter box. The server may perform computations of the data, for example, to determine an animal event, a motion of the animal, a signature of the animal, and the like. The server may be configured to communicate the data to the user and/or to one or more other parties (e.g., a veterinarian, spouse, etc.). In examples, a portable electronic device may perform computations of the data, for example, to determine an animal event, a motion of the animal, a signature of the animal, and the like. The portable electronic device may be configured to communicate the data to the user and/or one or more other parties (e.g., a veterinarian, spouse, etc.).

The activity collar may have a biometric monitoring sensor. The biometric monitoring sensor may be configured to determine body measurements and/or calculations of the animal. For example, temperature sensor and/or heart rate sensor may be used to determine the body temperature of the animal and/or the heart rate of the animal. The biometric monitoring sensor may be located on the activity collar or on another device position on or about the animal.

Figure 3:
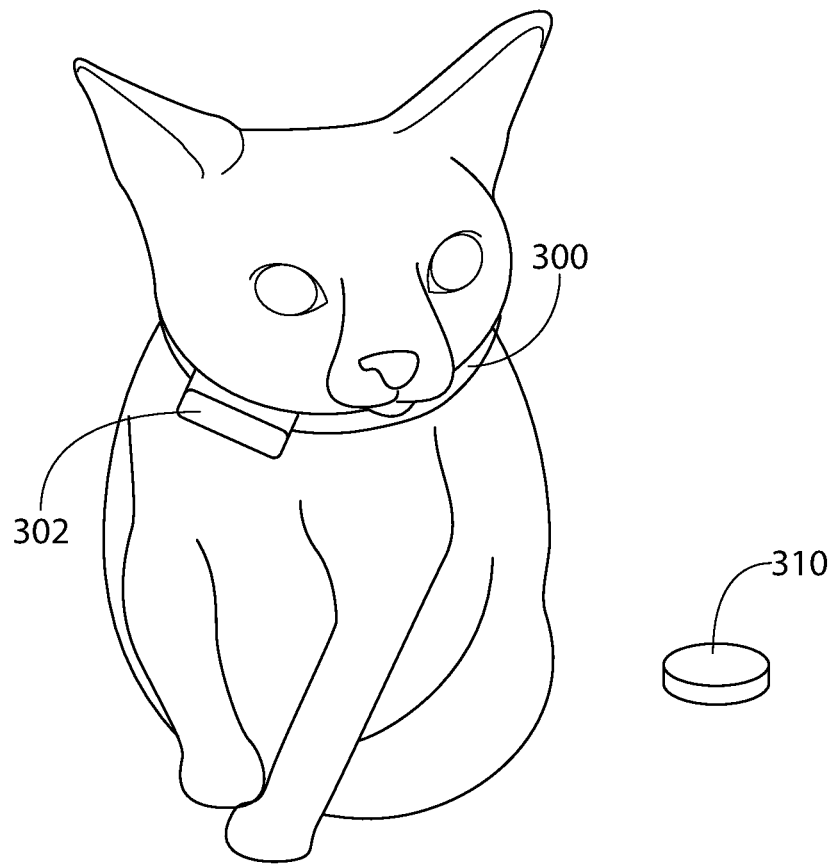
FIG. 3 is a depiction of an animal wearing the example activity collar of FIG. 2.

FIG. 3 shows an example use of the activity collar 300. As shown on FIG. 3, an animal (a cat) is wearing the activity collar 300. Although the example shown on FIG. 3 is a collar, it should be understood that the activity collar is for illustration purposes only and may be any wearable device that may come in other form factors besides a collar. For example, activity collar may be a jacket, vest, hat, gloves, contact lenses, rings (e.g., earrings), or any other device (or combinations of devices) that can be worn on the outside (or inside) of an animal.

As described herein, the activity collar 300 may have one or more sensors 302, such as an accelerometer. The sensor 302 may be coupled to the activity collar, for example, on an outside of the activity collar 300. In other examples, the sensor (e.g., accelerometer) may be integrally formed within the activity collar 300. As shown on FIG. 3, a location sensor 310 may be included in the system. The location sensor 310 may be located on the animal (e.g., worn by the animal) or positioned upon a surface that is not the animal. The location sensor 310 may be a proximity sensor. For example, a proximity sensor may be used to determine if the animal is near a predefined area, such as a feeding bowl, water bowl, and/or waste area.

The sensors and other devices may be used to determine whether an animal is performing an animal event (e.g., a urination, defecation, drinking, eating, resting, sleeping, etc.). An animal's urination and/or defecation behaviors and/or habits may be determined based on motion data, orientation data, location data, etc., of the animal. For example, if an animal's head is pointed in an upward direction, such as in a crouching posture, it may be determined that the animal is defecating. If the animal's leg is moving in a back and forth motion, and the position of the animal is unchanged, it may be determined that the animal is digging. The animal may be digging prior to a defecation.

The sensors and other devices may be used to determine the location at which an animal is performing an animal event (e.g., a urination, defecation, drinking, eating, resting, sleeping, etc.). The location at which the animal is performing the animal event may be useful for determining whether the animal is healthy or unhealthy. The location at which the animal is performing the animal event may be useful for determining whether the animal is exhibiting desired behaviors or undesired behaviors. The location at which the animal is performing the animal event may be useful for determining whether the animal is performing behaviors at desired or undesired locations.

For example, an animal resting in the middle of a room may be determined to be healthy and/or may be determined to be performing a desired behavior. An animal resting under a couch may be determined to be unhealthy and/or may be determined to be performing undesired behaviors (e.g., exhibiting a hiding behavior). An animal defecating in as designated area (e.g., a litter box) may be determined to be healthy and/or may be determined to be performing a desired behavior. An animal defecating in an area other than a designated waste area may be determined to be unhealthy (e.g. may have sudden diarrhea) and/or may be determined to be performing an undesired behavior. An animal resting in a designated resting area (e.g., a cat bed) may be determined to be healthy and/or may be determined to be performing a desired behavior. An animal resting on an area other than a designated area (e.g., the dinner table) may be determined to be unhealthy and/or may be determined to be performing an undesired behavior. An animal eating at a designated eating area (e.g., from a food bowl) may be determined to be healthy and/or may be determined to be performing a desired behavior. An animal eating at an area other than the designated area (e.g., from the garbage can) may be determined to be unhealthy and/or may be determined to be performing an undesired behavior.

The animal's urination and/or defecation may be determined based on location data. For example, if the animal is positioned within and/or about a designated waste area, such as a litter box, it may be determined that the animal is urinating or defecating. The animal's urination and/or defecation may be determined based on a combination of motion data and location data. For example, if the animal is near the waste area and the head of the animal is pointed in a crouching posture, it may be determined that the animal is defecating. The animal's urination and/or defecation may be determined based on a combination of more than one set of motion data. For example, if the head of the animal is pointed in a crouching posture, and the position of the animal is unchanged, it may be determined that the animal is defecating.

As provided herein, the activity collar may provide motion data, orientation data, etc., of the animal. In addition, a location data of the animal may be provided, for example, via a proximity sensor. The motion data, orientation data, and/or location data may be provided via devices worn by, or not worn by, the animal.

Figure 4A:
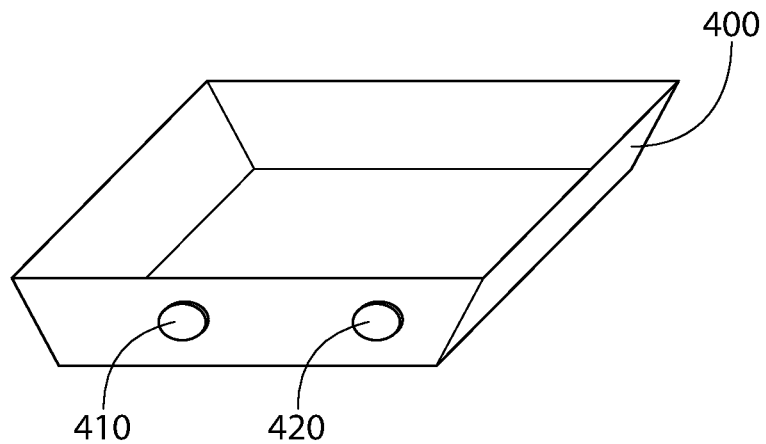
FIG. 4A is a perspective view of an example waste area having a sensor located on the waste area.
Figure 4B:
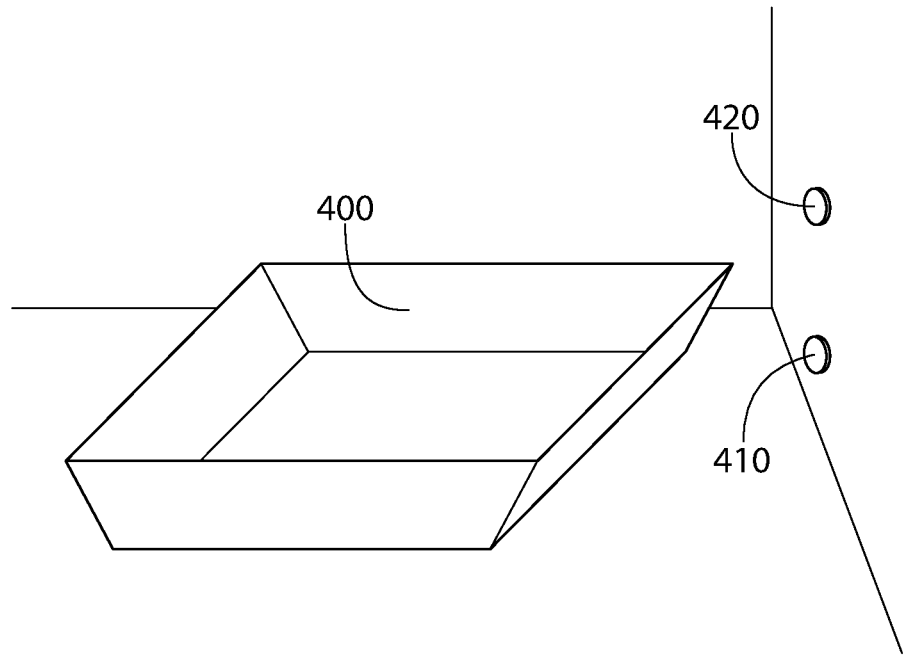
FIG. 4B is a perspective view of an example waste area with a sensor not located on the waste area.

FIGS. 4A, 4B the show example waste areas that may be used to monitor an animal's behaviors or habits, for example, to determine a health condition of the animal. A waste area may be any area that an animal uses for emptying its bowels, bladder, and a combination thereof regularly, periodically or occasionally. FIG. 4A shows an example waste area 400 (waste area 400) that includes one or more devices, such as a proximity sensor and measuring device. The proximity sensor may be a camera, scale, a motion detector, an RFID tag, an RFID reader, a GPS, a passive infrared, a microwave, an ultrasound, etc. The proximity sensor may be used to track the behavior or urination/defecation habits of the animal, for example, over a predefined time.

The animal's behaviors and/or habits relating to the animal's urination and/or defecation may be monitored at the waste area 400 using the sensors, devices (e.g., measuring devices), etc., located at or on the waste area. The animal's behaviors and/or habits relating to the animal's urination and/or defecation may also, or alternatively, be monitored at the waste area using the sensors, devices (e.g., measuring devices), etc., located on an animal (e.g., an activity collar), as described herein. The litter box 400 may track the times the litter box is used, the number of uses, and the duration of uses. The waste area 400 is shown as a litter box, however, it should be understood that a waste area may be form factors other than a litter box. For example, a waste area may be a designated area (e.g., inside a house or outside) in which an animal may defecate and/or urinate, including a backyard, a papered area, a toilet, a case (such as a birdcage, etc.).

As shown on FIG. 4A, waste area 400 waste area 400 may be an area designated for an animal (e.g., a cat) to urinate and/or defecate. Waste area 400 may have one or more sensors. The one or more sensors may be example sensor 410, shown on FIGS. 4A and 4B. As shown on FIG. 4A, sensor 410 may be located on a portion of the waste area, such as waste area 400. Sensor 410 may not be located on a portion of the waste area. For example, as shown on FIG. 4B, sensor 410 may be located on a wall, a table, etc., or any other surface that may be in a predefined proximity to the waste area. Sensor 410 may be a motion sensor (such as an accelerometer, a gyroscope, a magnetometer, etc.), a proximity sensor, an orientation sensor, a location sensor, and/or one or more other sensors, as described herein. Waste area 400 may include communication circuitry, such as blue tooth, RFID, Wi-Fi and other wireless technologies. Waste area 400 may communicate with an activity collar (such as activity collar 300) and/or a server. Waste area 400 may communicate directly with a portable electronic device of the user, or such communication may occur indirectly via a server and an application, such as a web application.

As described herein, waste area 400 may include a proximity sensor, such as a camera, scale, etc., to track the behavior or urination and/or defecation habits of the animal over time. The waste area 400 may include a delay to minimize incidences of false approaches (e.g., where an animal is merely walking by the waste area 400, as opposed to approaching the waste area 400 to urinate and/or defecate). The waste area 400 may include a memory, controller, and local user interface/display. The animal's behaviors and/or habits relating to the animal's urination and/or defecation may also, or alternatively, be monitored at the waste area using the sensors, devices (e.g., measuring devices), etc., located on an animal (e.g., an activity collar), as described herein.

Waste area 400 may have a measuring device, such as measuring device 420. As described herein, measuring device 420 may be one or more weighing scales, weight transducers, force transducers, displacement transducers, pressure transducers, weight sensors, force sensors, displacement sensors, pressure sensors, real time clocks, timers, counters, and/or a combination thereof. Measuring device 420 may be used to measure the weight and/or pressure of an animal located at or near a waste area. Measuring device 420 may be used to measure one or more weights, pressures, etc., at the waste area or around the waste area. For example, the measure device 420 may be used to measure the weight of an animal in the litter box, materials excreted from the animal (e.g., feces or urine excreted from the animal), etc., including a combination thereof. The measuring device 420 may be used to measure a pressure of the animal, for example, so that the measuring device can identify when an animal has entered the waste area.

Figure 5A:
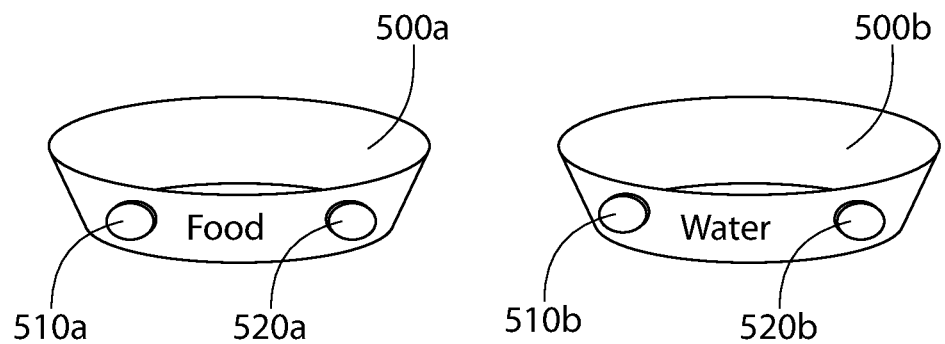
FIG. 5A is a perspective view of an example feeding dish and drinking bowl having a sensor located on the feeding bowl and drinking bowl.
Figure 5B:
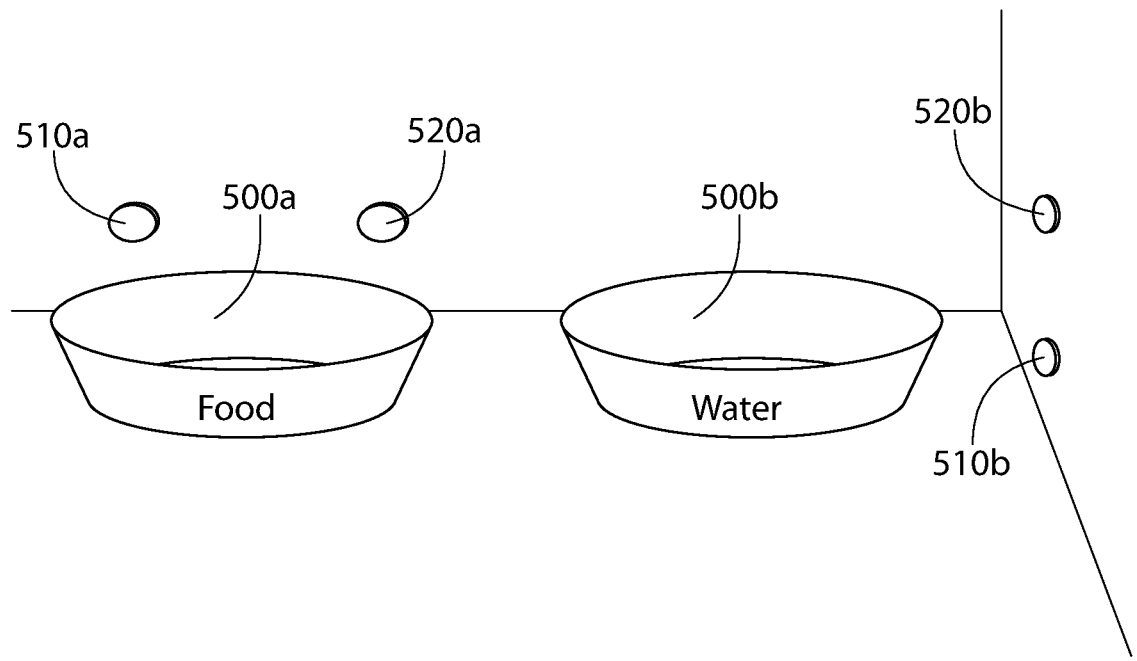
FIG. 5B is a perspective view of an example feeding dish and drinking bowl with a sensor not located on the feeding bowl or drinking bowl.

FIGS. 5A, 5B show example feeding and drinking areas that may be used to monitor an animal's behaviors or habits, for example, to determine a health condition of the animal. The animal's behaviors and/or habits relating to the animal's eating and/or drinking may be monitored at the feeding and/or drinking areas using the sensors, devices (e.g., measuring devices), etc., located at the feeding and/or drinking area. For example, feeding bowl 500a and/or drinking bowl 500b may include communication circuitry, such as blue tooth, RFID, Wi-Fi and other wireless technologies. The feeding bowl 500a and/or drinking bowl 500b may communicate with an activity collar (such as activity collar 300) and/or a server. Feeding bowl 500a and/or drinking bowl 500b may communicate directly with a portable electronic device of the user, or such communication may occur indirectly via a server and an application, such as a web application.

The feeding bowl 500a and/or drinking bowl 500b may include a proximity sensor, such as a camera, scale, etc., to track the behavior or eating and/or drinking habits of the animal over time. The feeding bowl 500a and/or drinking bowl 500b may include a delay to minimize incidences of false approaches (e.g., where an animal is merely walking by the feeding bowl 500a and/or drinking bowl 500b, as opposed to approaching the feeding bowl 500a and/or drinking bowl 500b to eat and/or drink). The feeding bowl 500a and/or drinking bowl 500b may include a memory, controller, and local user interface/display. The animal's behaviors and/or habits relating to the animal's feeding and/or drinking may also, or alternatively, be monitored at the feeding and/or drinking area using the sensors, devices (e.g., measuring devices), etc., located on an animal (e.g., an activity collar), as described herein. Although the feeding and/or drinking area is shown as a feeding bowl 500 and a drinking bowl 500b, it should be understood that a feeding and/or drinking bowl may be different form factors than shown on FIGS. 5A, 5B. For example, a drinking apparatus may include any device used by the animal to eat and/or drink. For example, the drinking apparatus may be a water bottle (e.g., as used by a guinea pig, bunny), a sponge, an elevated pool, etc.

As shown on FIG. 5A, food dish 500a and/or a drinking bowl 500b may be an area designated for an animal (e.g., a cat) to eat and/or drink. The food dish 500a and/or drinking bowl 500b may have one or more sensors. For example, a sensor may be located on the food dish and the water bowl, the food dish and not the water bowl, or vice-versa. The one or more sensors may be example sensors 510a, 510b, shown on FIGS. 5A and 5B. As shown on FIG. 5A, sensors 510a, 510b may be located on a portion of the eating and/or drinking area, such as on food dish 500a and/or a drinking bowl 500b. Sensors 510a, 510b may not be located on a portion of the eating and/or drinking area. For example, as shown on FIG. 5B, sensors 510a, 510b may be located on a wall, a table, etc., or any other surface that may be in a predefined proximity to the eating and/or drinking area. Sensors 510a, 510b may be one or more motion sensors (such as an accelerometer, a gyroscope, a magnetometer, etc.), proximity sensors, orientation sensors, location sensors, and/or one or more other sensors, as described herein.

Food dish 500a and/or a drinking bowl 500b may have a measuring device, such as measuring devices 520a, 520b. As described herein, measuring devices 520a, 520b may be one or more weighing scales, weight transducers, force transducers, displacement transducers, pressure transducers, weight sensors, force sensors, displacement sensors, pressure sensors, real time clocks, timers, counters, and/or a combination thereof. Measuring device may be used to measure the weight and/or pressure of the animal at or near the eating and/or drinking area, in an example. Measuring device may be used to measure the weight and/or pressure of food and/or drink located at or near the eating and/or drinking area. Measuring devices 520a, 520b may be used to measure one or more weights, pressures, etc., at the eating and/or drinking area or around the eating and/or drinking area.

Measuring device 520a may be used to measure the weight of the food in food dish 500a. A computation may be performed to determine the amount of food eaten (or not eaten) from the food dish 500a. The measuring device 520b may be used to measure the weight of the liquid in the drinking bowl 500b. A computation may be performed to determine the amount of liquid consumed (or not consumed) from the drinking bowl 500b. Based on the weight (e.g., the change of weight) of the food dish 500a and/or drinking bowl 500b, it may be determined if the animal is eating and/or drinking. For example, if the weight of the food dish 500a and/or drinking bowl 500b is steadily decreasing, it may be determined that the animal is eating from the respective food dish 500a and/or drinking bowl 500b. A health condition of the animal may be determined based on the amount of food and/or liquid consumed by the animal. For example, if the animal is eating and/or drinking less than an amount typically consumed by a healthy animal, the animal may be determined to be unhealthy (e.g., injured, ill, diseased, etc.). If the animal is eating and/or drinking more than an amount typically consumed by a healthy animal, the animal may be determined to be unhealthy. In other examples, if the animal is eating and/or drinking more than an amount typically consumed by a healthy animal, the animal may be determined to be recovering from an unhealthy condition.

As described herein, the animal's eating, drinking, urination, defecation, and/or rest may be determined based on motion data (e.g., if one or more parts of the animal are moving), orientation data (e.g., if one or more parts of the animal, such as the animal's head, is pointed in a downward direction). The animal's eating, drinking, urination, defecation, and/or rest may be determined based on location data (e.g., if the animal is near the waste area, the eating area, the drinking area, the resting area (e.g., a bed), etc. The animal's eating, drinking, urination, defecation, and/or rest may be determined based on a combination of location data and motion data (e.g., if the animal is near the food dish and the head is pointed towards a food dish).

Based on one or more of the animal's motion, location, orientation, etc., a signature of an activity of the animal may be determined. An animal event (e.g., whether an animal is urinating, defecating, eating, drinking, and/or resting) may be determined based on one or more signatures of the animal. The signatures of the animals may be a scratching, turning (e.g., in circles), a crouching, a sniffing, a defection posture, a urination posture, a peristaltic movement, and the like. Unsuccessful urinations and/or successful urinations may be determined via a signature. Unsuccessful defecations and/or successful defecations may be determined via a signature. Signatures may be used to determine a non-event, such as an event proximate to the feeding, drinking, waste, and/or rest area that aren't related to eating, drinking, urinating, defecating, and/or resting, respectively.

A signature of urinating and/or defecating may include a scratching and/or digging. For example, a scratching and/or digging may be determined based on a location of the animal near or in the waste area (e.g., litter box). The location of the animal may be determined via a proximate sensor, a measurement device (e.g., a scale weighing a litter box), a motion sensor, or one or more other devices. The orientation of the animal may be used to determine a scratching and/or digging. For example, if the animal is oriented towards a ground (e.g., towards a litter) a scratching and/or digging may be indicated. A digging movement of the animal may indicate a scratching and/or digging. The movement of the animal may be determined via one or more sensors, such as one or more accelerometers, gyroscopes, magnetometers, etc. For example, a leg moving in a back and forth motion may indicate a scratching and/or digging.

A signature of urinating and/or defecating may include the animal turning in circles. For example, a turning in circles may be determined based on a location of the animal near or in the waste area (e.g., litter box). The location of the animal may be determined via a proximate sensor, a measurement device (e.g., a scale weighing a litter box), a motion sensor, or one or more other devices. The orientation of the animal may be used to determine a turning in circles. For example, if the orientation of the animal indicates a circular movement/motion, a turning in a circle may be indicated.

A signature of urinating and/or defecating may include a crouching of the animal. For example, a crouching of the animal may be determined based on a location of the animal near or in the waste area (e.g., litter box). The location of the animal may be determined via a proximate sensor, a measurement device (e.g., a scale weighing a litter box), a motion sensor, or one or more other devices. The orientation of the animal may be used to determine a crouching of the animal. For example, if the animal is oriented towards a ground (e.g., towards a litter) a crouching of the animal may be indicated. A lack of movement of the animal may indicate a crouching of the animal. For example, if the position of the animal remains unchanged (e.g., the animal is stationary, the animal is not digging/scratching), a crouching of the animal may be indicated. The movement of the animal may be determined via one or more sensors, such as one or more accelerometers, gyroscopes, magnetometers, etc.

A signature of urinating, defecating, eating, and/or drinking may include a sniffing. For example, a sniffing may be determined based on a location of the animal near or in the waste area (e.g., litter box) or feeding/drinking area. The location of the animal may be determined via a proximate sensor, a measurement device (e.g., a scale weighing a litter box), a motion sensor, or one or more other devices. The orientation of the animal may be used to determine a sniffing of the animal. For example, if the animal is oriented towards a ground (e.g., towards a litter) a sniffing of the animal may be indicated. The animal being in a stationary position may indicate a sniffing. A movement of the head of the animal (e.g., an up and down movement of the animal's head) may indicate a sniffing. For example, if the position of the animal remains unchanged (e.g., the animal is stationary, the animal is not digging/scratching), a crouching of the animal may be indicated. The movement of the animal may be determined via one or more sensors, such as one or more accelerometers, gyroscopes, magnetometers, etc.

A signature of a defecating may include the animal being in a defecating posture. For example, a defecating posture may be determined based on a location of the animal near or in the waste area (e.g., litter box). The location of the animal may be determined via a proximate sensor, a measurement device (e.g., a scale weighing a litter box), a motion sensor, or one or more other devices. The orientation of the animal may be used to determine a defecating posture. For example, if the head of the animal is oriented upright and/or in a forward direction a defecating posture may be indicated. A movement of the animal in a side to side direction (e.g., to spread the animal's hind legs) may indicate a defecating posture. A lifting of a tail may indicate a defecating posture. Peristaltic movements (e.g., a back and forth motion) may indicate a defecating posture. A digging motion, for example, prior to and/or before one or more of the actions described above, may indicate a defecating posture.

A signature of a urinating may include the animal being in a urinating posture. For example, a urinating posture may be determined based on a location of the animal near or in the waste area (e.g., litter box). The location of the animal may be determined via a proximate sensor, a measurement device (e.g., a scale weighing a litter box), a motion sensor, or one or more other devices. The orientation of the animal may be used to determine a urinating posture. For example, if the head of the animal is oriented upright and/or in a forward direction a urinating posture may be indicated. A movement of the animal in a side to side direction (e.g., to spread the animal's hind legs) may indicate a urinating posture. A lifting of a tail may indicate a urinating posture. A lack of peristaltic movements (e.g., a back and forth motion) may indicate a urinating posture. A digging motion, for example, prior to and/or before one or more of the actions described above, may indicate a urinating posture.

A signature of urinating and/or defecating may include peristaltic movements. For example, peristaltic movements may be determined based on a location of the animal near or in the waste area (e.g., litter box). The location of the animal may be determined via a proximate sensor, a measurement device (e.g., a scale weighing a litter box), a motion sensor, or one or more other devices. A peristaltic movement may be a back and forth motion (e.g., a slight back and forth motion) of the animal. For example, a peristaltic movement may be a jumping in and/or out of a litter box.

A signature of a successful defecation may include one or more activities and/or characteristics of the animal. For example, a successful defecation may be determined based on a location of the animal near or in the waste area (e.g., litter box). The location of the animal may be determined via a proximate sensor, a measurement device (e.g., a scale weighing a litter box), a motion sensor, or one or more other devices. The orientation of the animal may be used to determine a successful defecation. For example, if the head of the animal is oriented upright and/or in a forward direction a successful defecation may be indicated. A movement of the animal in a side to side direction (e.g., to spread the animal's hind legs) may indicate a successful defecation. A lifting of a tail may indicate a successful defecation. Peristaltic movements (e.g., a back and forth motion) may indicate a successful defecation. A digging motion, for example, prior to and/or before one or more of the actions described above, may indicate a successful defecation. Following one or more of the above actions with a sniffing and/or a digging may indicate a successful defecation. A weight change in the litter box may indicate a successful defecation. The weight change may be indicated via a measurement device, such as a weighing scale. The animal quickly leaving the waste area after performing one or more of the above actions may indicate a successful defecation.

A signature of an unsuccessful defecation may include one or more activities and/or characteristics of the animal. For example, an unsuccessful defecation may be determined based on a location of the animal near or in the waste area (e.g., litter box). The location of the animal may be determined via a proximate sensor, a measurement device (e.g., a scale weighing a litter box), a motion sensor, or one or more other devices. The orientation of the animal may be used to determine an unsuccessful defecation. For example, if the head of the animal is oriented upright and/or in a forward direction an unsuccessful defecation may be indicated. A movement of the animal in a side to side direction (e.g., to spread the animal's hind legs) may indicate an unsuccessful defecation. A lifting of a tail may indicate an unsuccessful defecation. A lack of peristaltic movements (e.g., a back and forth motion) may indicate an unsuccessful defecation. A digging motion, for example, prior to and/or before one or more of the actions described above, may indicate an unsuccessful defecation. Following one or more of the above actions with a sniffing and/or a digging may indicate an unsuccessful defecation. A lack of weight change in the litter box may indicate an unsuccessful defecation. A weight change (or a lack of weight change) may be indicated via a measurement device, such as a weighing scale. The animal remaining in the waste area for a predetermined amount of time (e.g., a period of time determined to be later than typically used for a successful defecation) may indicate an unsuccessful defecation. The animal being restless may indicate an unsuccessful defecation. For example, the animal moving and/or rearranging its posture and/or reassuming a position (e.g., a squatting position) multiple times may indicate an unsuccessful defecation. Repeated visits to the waste area may indicate an unsuccessful defecation.

A signature of a successful urination may include one or more activities and/or characteristics of the animal. For example, a successful urination may be determined based on a location of the animal near or in the waste area (e.g., litter box). The location of the animal may be determined via a proximate sensor, a measurement device (e.g., a scale weighing a litter box), a motion sensor, or one or more other devices. The orientation of the animal may be used to determine a successful urination. For example, if the head of the animal is oriented upright and/or in a forward direction a successful urination may be indicated. A movement of the animal in a side to side direction (e.g., to spread the animal's hind legs) may indicate a successful urination. A lifting of a tail may indicate a successful urination. A backward motion of the animal and/or a tail twitch may indicate a successful urination. A lack of peristaltic movements (e.g., a back and forth motion) may indicate a successful urination. A digging motion and/or sniffing, for example, prior to and/or before one or more of the actions described above, may indicate a successful urination. The animal being at the waste area for a short period of time may indicate a successful urination. A weight change in the litter box may indicate a successful urination. The weight change may be indicated via a measurement device, such as a weighing scale.

A signature of an unsuccessful urination may include one or more activities and/or characteristics of the animal. For example, an unsuccessful urination may be determined based on a location of the animal near or in the waste area (e.g., litter box). The location of the animal may be determined via a proximate sensor, a measurement device (e.g., a scale weighing a litter box), a motion sensor, or one or more other devices. The orientation of the animal may be used to determine an unsuccessful urination. For example, if the head of the animal is oriented upright and/or in a forward direction an unsuccessful urination may be indicated. A movement of the animal in a side to side direction (e.g., to spread the animal's hind legs) may indicate an unsuccessful urination. A lifting of a tail may indicate an unsuccessful urination. A backward motion of the animal and/or a tail twitch may indicate an unsuccessful urination. A lack of peristaltic movements (e.g., a back and forth motion) may indicate a successful urination. A digging motion, for example, prior to and/or before one or more of the actions described above, may indicate an unsuccessful urination. The animal being at the waste area for a long period of time may indicate an unsuccessful urination. A lack of weight change in the litter box may indicate an unsuccessful defecation. The animal being restless may indicate an unsuccessful urination. For example, the animal moving and/or rearranging its posture and/or reassuming a position (e.g., a squatting position) multiple times may indicate an unsuccessful urination. Repeated visits to the waste area may indicate an unsuccessful urination.

A signature of a non-event may include one or more characteristics of the animal and/or the waste area. A non-event may include the animal passing through the waste area, an object (e.g., an animal toy) falling into waste area, a shadow being shown across the waste area, etc. A non-event may be indicated via a lack of weight change in waste area (e.g., the litter box). In addition, a non-event may be indicated based on the lack of one or more activities and/or characteristics described above for the signatures of an animal urinating and/or defecating.

A signature of an eating may include a chewing. For example, a chewing may be determined based a head movement of the animal, such as a repeated up, down, back, and/or forward head movement of the animal. A chewing may be determined based on a crouching posture, as described herein. A chewing may be determined based on a location of the animal near or at a feeding area (e.g., at a food dish).

A signature of a drinking may include a lapping. For example, a lapping may be determined based a head movement of the animal, such as a repeated head movement of the animal. A lapping may be determined based on an orientation of an animal's head, such as the animal's head being oriented downward. A lapping may be determined based on a location of the animal near or at a drinking area (e.g., at a drinking bowl).

A signature of an eating and/or drinking may include a swallowing. For example, a swallowing may be determined based a chewing motion, such as repetitive up and/or down crunching motions of the animal. A swallowing may be determined based on muscular contractions (e.g., large muscular contractions) of the animal. A swallowing may be determined based on repeated movements of the animal, for example, over a period of time. A swallowing may be determined based on a location of the animal near or at a drinking area and/or a feeding area.

A signature of cleaning of the animal may include a licking. For example, a licking may be determined based on a repeated motion of the head of the animal. A licking may be determined based on an orientation of a head of the animal and/or a change of orientation of the head of the animal. For example, a licking may be determined based on a head of the animal being positioned downwards or turned towards the body of the animal.

A signature of an eating may include a retracting the head of the animal from the bowl, for example, to chew. For example, a retraction of the head from the bowl to chew may be determined based a head movement of the animal. A retraction of the head from the bowl to chew may be determined based on an orientation of the animal's head, such as the head posture changing from upwards to downwards. A chewing may be determined based on a location of the animal near or at a feeding area (e.g., at a food dish).

A signature of being active or inactive may include a climbing. For example, a climbing may be determined based a jumping movement (e.g., an initial jumping movement) of the animal. A climbing may be determined based on high energy movements of the animal, for example, for the duration of the climbing event. A climbing may be determined based on a transition of the animal to a walking behavior or a stationary behavior.

A signature of being active or inactive may include a jumping. For example, a jumping may be determined based a short, high energy movement of the animal. A jumping may be determined based on a transition of the animal to a walking behavior or a stationary behavior. A jumping may be determined based on change in head posture (e.g., looking up/down) of the animal, for example, prior to a jump.

A signature of a cleaning may include a licking (e.g., grooming). For example, a licking may be determined based a repeated motion of the animal's head. A licking may be determined based on an orientation of the animal's head, for example, a head positioned downwards or turned towards the animal's body.

A signature of being ill or diseased may include a vomiting. For example, a vomiting may be determined based on a movement (e.g., repeated movements back and forth) of the animal. A vomiting may be determined based on muscular contractions of the animal. Vomiting may be determined based on a subsequent licking, grooming, and/or swallowing of the animal. Vomiting may be based on an orientation, such as the head of the animal being turned downwards.

A signature of resting (e.g., being inactive) may include a sleeping. For example, a sleeping may be determined by a period (e.g., long period) of lack of activity and/or a short period (e.g., seconds) of increased activity. The activity of the animal may be based on a movement of the animal, such as a running, jumping, playing, etc., of the animal. A sleeping may be determined based on a location of the animal (e.g., at a favorite location of the animal).

A signature of being inactive may include a resting. For example, a resting may be determined by a period (e.g., long period) of lack of activity. The period of lack of activity may be followed by a short period (e.g., seconds) of increased activity. The activity of the animal may be based on a movement of the animal, such as a running, jumping, playing, etc., of the animal. A resting may be determined based on a location of the animal (e.g., at a favorite location of the animal).

One or more diseases, illness, injuries, etc., of the animal may be detected based on an eating, drinking, urinating, defecating, and/or resting of the animal. A signature of an illness (e.g., being sick, being diseased, etc.) may include having Feline Idiopathic Cystitis (FIC). FIC may be determined based on one or more activities of the animal. For example, FIC may be determined based on an unsuccessful attempt to urinate, repeated/frequent attempts to urinate, a vocalization while the animal is urinating, licking (e.g., excessive licking) of the genital area, for example, in between urination attempts, and/or attempts to urinate outside of/away from litter box.

A signature of an illness, disease, etc., may include the animal having diarrhea. Diarrhea may be determined based on attempts to defecate, as described herein. The attempts to defecate may include successful or unsuccessful attempts to defecate, and/or repeated/frequent attempts to defecate. Diarrhea may be determined based on the animal vocalizing while defecating. Diarrhea may be determined based on the animal straining and/or being restless during attempts to defecate. Diarrhea may be determined based on licking (e.g., excessive licking) of the animal's genital area between defecation attempts. Diarrhea may be determined based on a location of the animal. For example, diarrhea may be determined based on the animal attempting to defecate outside and/or away from the animal's waste area, such as away from a cat's litter box.

A signature of an illness, disease, etc., may include the animal being constipated. Constipation may be determined based on a motion of the animal and/or actions of the animal. For example, constipation may be determined based on the animal dragging its bottom, for example, on or across a floor. Constipation may be determined based on the animal vomiting, as described herein. Constipation may be determined based on the animal drinking and/or eating less than the animal drinks and/or eats. Constipation may be determined based on the animal drinking and/or eating less than a healthy animal typically drinks and/or eats. Constipation may be determined based on the animal hiding, which may be determined based on the animal positioning itself in a location remote from others and/or which is different than where the animal typically positions itself. Constipation may be determined based on attempts of the animal to defecate, as described herein. Constipation may be determined based on the animal vocalizing while defecating. Constipation may be determined based on the animal straining and/or being restless during attempts to defecate. Constipation may be determined based on licking (e.g., excessive licking) of the animal's genital area between defecation attempts. Constipation may be determined based on the animal attempting to defecate outside and/or away from the animal's waste area, such as away from a cat's litter box.

A signature of an illness, disease, etc., may include the animal having diabetes. Diabetes may be determined based on the animal having an increased thirst (e.g., drinking more than the animal typically drinks or more than a healthy animal typically drinks) and/or urinating an increased amount of times. Diabetes may be determined based on the animal changing its eating habits, such as eating more than typical or eating less than typical. Diabetes may be determined based on the animal having weak legs, such as weak hind legs. Weak hind legs may be determined based on the animal reducing its jumping activities, spending less time in its favorite elevated areas, and/or changes in the animal's walking and/or climbing motions.

A signature of an illness, disease, etc., may include the animal having a disease of a kidney. A disease of a kidney may be determined based on the animal having an increased thirst (e.g., drinking more than the animal typically drinks or more than a healthy animal typically drinks) and/or urinating an increased amount of times. A disease of a kidney may be determined based on the animal changing its eating habits, such as eating less than typical. A disease of a kidney (e.g., bacterial infections of the kidney and/or bladder) may be determined based on the animal unsuccessfully attempting to urinate and/or licking of its genitals before or after a urination, urination attempt, defecation, and/or defecation attempt. A disease of a kidney may be based on a decreased activity of the animal.

A signature of an illness, disease, etc., may include the animal having hyperthyroidism. Hyperthyroidism may be determined based on an increased appetite of the animal, an increased thirst of the animal, and/or an increase in the activity of the animal (e.g., a restlessness of the animal). Hyperthyroidism may be determined based on a decrease in the animal's sleep. Hyperthyroidism may be determined based on the animal vomiting and/or having diarrhea, as described herein.

A signature of an illness, disease, etc., may include the animal having arthritis. Arthritis may be determined based on a motion of the animal and/or actions of the animal. For example, arthritis may be determined based on a decreased activity of the animal, a change in the animal's walking motion, a reduction of the animal jumping, and/or a change in the animal's climbing motion (e.g., a climbing of a tree, scratching post, stairs, etc.). Arthritis may be determined based on changes in the restlessness and/or sleep quality of the animal. Arthritis may be determined based on licking (e.g., excessive licking) of the animal's joints and/or other areas of the animal which may be in pain. Arthritis may be determined based on the animal spending less time in favorite areas (e.g., on top of cabinets, on top of furniture, on top of cat tree) of the animal which may be elevated. Arthritis may be determined based on the animal hiding (e.g., hiding under the couch, behind the washer/dryer, under the bed). Arthritis may be determined based on the amount of time spent at a location, the speed of the animal in getting to a location, the regularity with which the animal visits an area, etc.

A signature of an illness, disease, etc., may include the animal being in pain. Pain of the animal may be determined based on a motion of the animal and/or actions of the animal. For example, pain of the animal may be determined based on a decreased activity of the animal, a change in the animal's walking motion, a reduction of the animal jumping, and/or a change in the animal's climbing motion (e.g., a climbing of a tree, scratching post, stairs, etc.). Pain of the animal may be determined based on changes in the restlessness and/or sleep quality of the animal. Pain of the animal may be determined based on licking (e.g., excessive licking) of the animal's joints and/or other areas of the animal which may be in pain. Pain of the animal may be determined based on the animal spending less time in favorite areas (e.g., on top of cabinets, on top of furniture, on top of cat tree) of the animal which may be elevated. Pain of the animal may be determined based on the animal hiding (e.g., hiding under the couch, behind the washer/dryer, under the bed). Pain of the animal may be determined based on the amount of time spent at a location, the speed of the animal in getting to a location, the regularity with which the animal visits an area, etc.

Mathematical and/or algorithmic techniques, such as bivariate, multivariate and trend analysis, may be used to formulate a trend of the animal events (e.g., feeding, drinking, urinating, defecating, sleeping). Data collected over time and processed can represent a typical profile of behavior and habits of an animal. The behavior and habits of the animal may be used to determine the animal's health condition. For example, an injured or otherwise ill animal may exhibit different defecating habits than a healthy animal. Trend analysis may be used to determine whether the monitored behavior, habits, etc. of the animal are random, or whether a trend may be developing.

Data may be captured for the duration of the animal's activity inside a waste area, during food or water consumption, and/or during rest. Data may be captured by periodically sampling a sensor or sensors, such as a motion sensor (e.g., an accelerometer, gyroscope, or the like), a proximity sensor (e.g., such as a camera or the like), etc. An array of digital data may be processed, for example, to extract an animal event (e.g., feeding, urination, defecation, or rest of the animal). The data may be processed inside the device on-the-fly (e.g., applying methods as the data samples come in and not storing the entire data). Data may be stored in the device (in full length or a portion). Data may be processed with a delay, for example, in the device. Data may be processed externally from the device. For example, the data may be processed in a server, in a portable electronic device, and/or in a database that may perform the processing of the data.

Notifications may be delivered to the user, for example, in the form of an electronic mail message sent to a user-specified electronic mail address, a text message sent via SMS (Short Message Service) to a user-specified mobile phone number, a calendar reminder set up by the system in a user-specified calendar, phone calls to a user-specified mobile or landline phone number, messages by a mobile phone application of a user's mobile phone, etc.

The time and/or duration of an animal's time at a feeding area and/or a waste area may be recorded. For example, a date and/or time of the animal's visit to a waste area may be recorded. A time duration of the animal's presence inside the waste area may be recorded. The movements, orientations, and/or locations of the animal at a feeding area and/or a waste area may be recorded. All records may be stored and/or may be presented, for example, via a textual or graphical format.

A profile of the animal may be accessed via a portable electronic device. The portable electronic device may provide a user interface, for example, via an application downloaded on the portable electronic device. A user may create a profile associated with the animal. The application may display the animal's profile and/or may be facilitate the uploading of monitoring information of the animal. Icons or symbols displayed on the application may designate an animal event that is being monitored and/or tracked. For example, a feeding bowl may be displayed to show feeding information, a litter box may be displayed to show defecation/urination information. Such data may be displayed in graph form for ease of reference.

FIGS. 6A-6D show example screenshots of a use of the animal monitoring system. The screenshots may be provided on a portable electronic device, for example. The screenshots provide notifications to the user of animal events (e.g., urinations, defecations, feedings, drinkings) of the animal. The notifications and animal events shown on the screenshots are for illustration purposes only and are not limiting. In examples, other notifications and/or other animal events may be provided to the user.

Figure 6A:
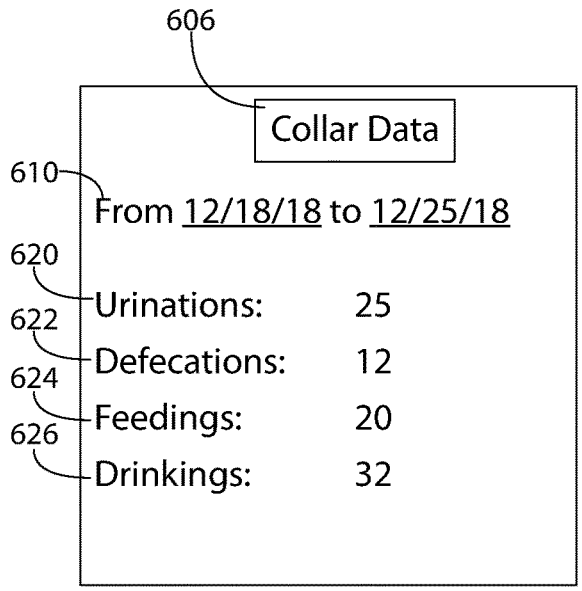
FIGS. 6A-6D are example screenshots of a use of the system of FIG. 1.

FIG. 6A shows an example screen shot of data collected by an activity collar (such as activity collar 200) worn by an animal. Category 606 shows the category of the data provided on the screen (e.g., data being related to the activity collar). In other examples, category 606 may show other categories, including categories relating to the animal's eating/drinking area, waste area, rest area, etc., or a combination thereof. Data of the animal event (e.g., urinating, defecating, eating, drinking, resting), signatures of the animal event (e.g., digging, crouching, taking a certain posture), motions of the animals (e.g., moving a leg, remaining in a static position) may be provided via one or more screenshots. The screenshots may be provided on a display, such as on a display of a portable electronic device.

As shown on FIGS. 6A-6D, a time period 610 may be provided. Time period 610 may define the period of the data provided (e.g., the period in which the animal event, etc., data will be provided). Using the example shown on FIG. 6A, the urination data 620, defecation data 622, feeding data 624, and/or drinking data 626 is provided on the time period 610 from Dec. 18, 2018 to Dec. 25, 2018. In other examples, time period 610 may be any time period, including a single day (e.g., Dec. 18, 2018). Based on the desired time period 610 provided on FIG. 6A, the urination data 620 is 25 times, defecation data 622 is 12, feeding data 624 is 20, and drinking data 626 is 32. The numbers of these events, and the listing of the events, is for illustration purposes only. Different (including more or less) categories of data, time periods, animal events, etc., may be displayed. For example, duration data of an animal even may be provided, determinations of successful and/or unsuccessful animal events may be provided, time periods of animal events may be provided, etc.

Figure 6B:
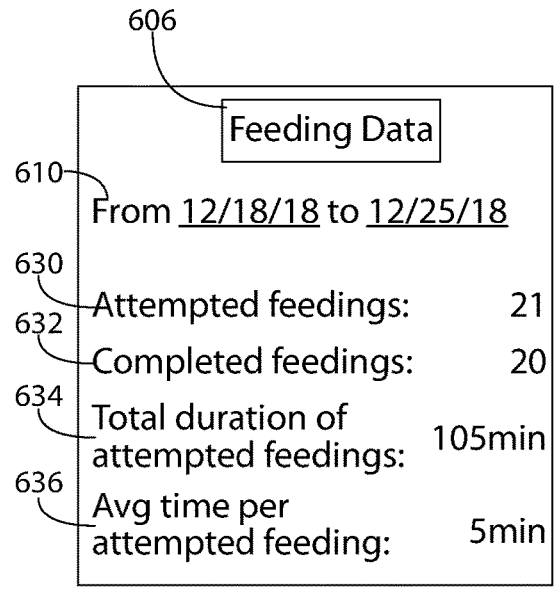

Using the example shown on FIG. 6B, category 606 may relate to feeding data. Feeding data may be provided on a time period 610, for example, from Dec. 18, 2018 to Dec. 25, 2018. As described herein, in other examples time period 610 may be any time period, including a single day (e.g., Dec. 18, 2018). Based on the desired time period 610, the feeding data may be provided, including the animal having 21 attempted feedings 630, 20 completed feedings 632, 105 minutes as the duration of the feedings 634, and five minutes of average time per feeding 636. As described herein, the numbers of these events, the listing of the events, etc., is for illustration purposes only. Different (including more or less) categories of data may be displayed.

Figure 6C:
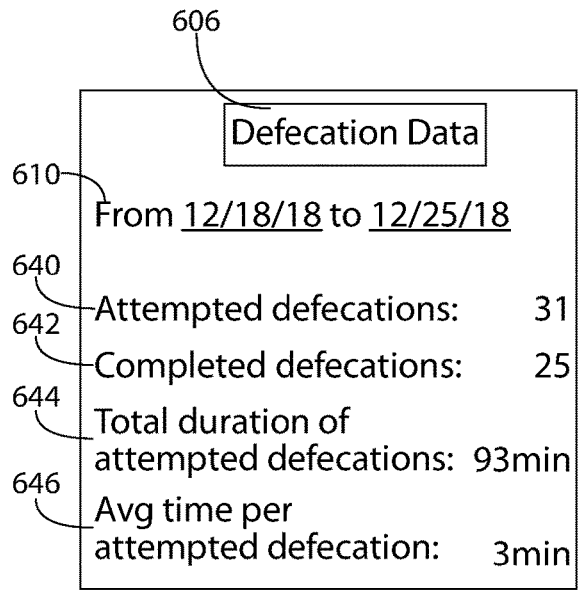

As shown on FIG. 6C, category 606 may relate to defecating data. Defecating data may be provided on a time period 610, for example, from Dec. 18, 2018 to Dec. 25, 2018. In other examples time period 610 may be any time period, including a single day (e.g., Dec. 18, 2018). Based on the desired time period 610, the defecating data may be provided, including the animal having 31 attempted defecations 640, 25 completed defecations 642, 93 minutes as the duration of the defecations 644, and three minutes of average time per defecation 646. As described herein, the numbers of these events, the listing of the events, etc., is for illustration purposes only. Different (including more or less) categories of data may be displayed.

Figure 6D:
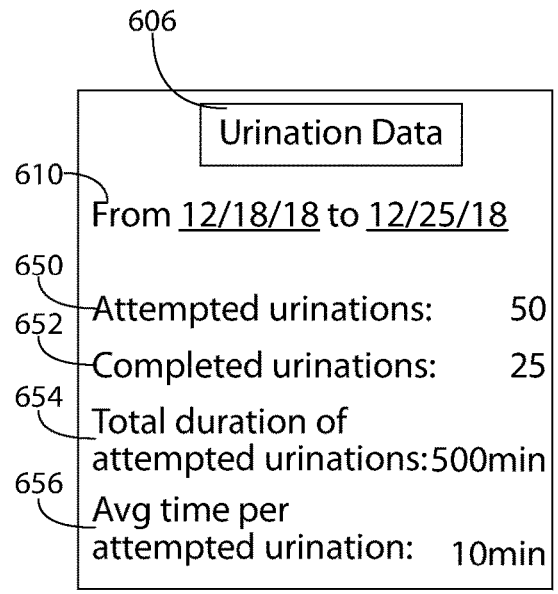

As shown on FIG. 6D, category 606 may relate to urination data. Urination data may be provided on a time period 610, for example, from Dec. 18, 2018 to Dec. 25, 2018. In other examples time period 610 may be any time period, including a single day (e.g., Dec. 18, 2018). Based on the desired time period 610, the urination data may be provided, including the animal having 50 attempted urinations 650, 25 completed urinations 652, 500 minutes as the duration of the urinations 654, and ten minutes of average time per urination 656. As described herein, the numbers of these events, the listing of the events, etc., is for illustration purposes only. Different (including more or less) categories of data may be displayed. More, or less, screen shots may be provided in which more or less data is presented to a user. The screenshots and/or data may be used for providing animal event data, signature data, motion data, orientation data, location data, etc., of the animal.

Figure 7:
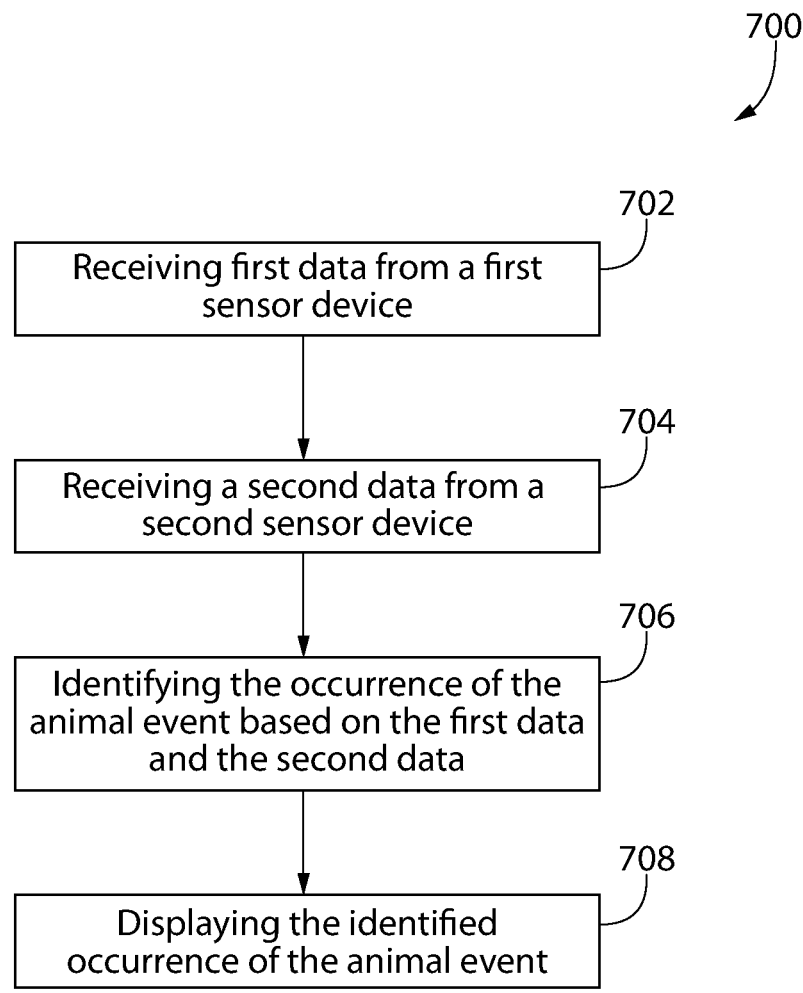
FIG. 7 is an example use of the system, as described herein.

Based on the above, a health condition of the animal may be provided. For example, if a healthy animal takes three minutes (e.g., approximately three minutes) per defecation, FIG. 6C may provide an indication that the animal's bowels are likely in working order and/or that the animal is not sick, injured, etc. Conversely, if a healthy animal takes one minute (e.g., approximately ten minutes) per urination, FIG. 6D may provide an indication that the animal's bladder may not be in working order. For example, because the animal is taking ten minutes (e.g., an average of ten times longer than normal) per urination, it may be determined that the animal has a bladder infection, an issue with an organ (e.g., a kidney), the animal is not drinking enough water, the animal is injured, etc. The data may be provided to the user of the portable device and/or an animal doctor for further diagnosis. Other data (such as drinking data in this example) may be used to see if there is a drinking anomaly in addition to the urination anomaly. For example, one or more other types of data may be used to confirm an anomaly in addition to the urination anomaly FIG. 7 describes an example method 700 of an animal monitoring. At 702, first data may be received from a first sensor. First data may also, or alternatively, be received from one or more other devices, such as a measuring device or one or more other sensors. The first data may be received at a processor.

The first sensor may be one or more sensors, as described herein. For example, the first sensor may be a sensor (or other device) configured to detect a location of the animal, to detect the motion (or stillness) of the animal, to detect an orientation of the animal, etc. The first sensor may be one or more of a variety of form factors, including, but not limited to, an accelerometer, a gyroscope, a magnetometer, weighing scales, weight transducers, force transducers, displacement transducers, pressure transducers, weight sensors, force sensors, displacement sensors, pressure sensors, load cells, photographic cameras, video cameras, camcorders, contact thermometers, non-contact thermometers, and a combination thereof. In addition, or alternatively, first sensor may be one or more of optical sensors, optical reflecting sensors, LED/photodiode pair optical sensors, LED/phototransistor pair optical sensors, laser diode/photodiode pair optical sensors, laser diode/phototransistor pair optical sensors, optocouplers, optical fiber coupled optical sensors, magnetic sensors, weight sensors, force sensors, displacement sensors, pressure sensors, various proximity sensors, such as inductive proximity sensors, magnetic proximity sensors, capacitive proximity sensors, and/or a combination thereof.

First data may be motion, location, orientation, etc., data of an animal. The motion, location, orientation, etc., data of the animal may be provided via one or more sensors or devices. The first data may be a signature of an animal event, as described herein. For example, the signature of the animal may be a scratching, turning (e.g., in circles), a crouching, a sniffing, a defection posture, a urination posture, a peristaltic movement, and the like. The signature may be associated with an animal event. For example, the signature may be associated with an animal's urination, defecation, drinking, eating, sleeping, and the like.

At 704, second data may be received from a second sensor. Second data may also, or alternatively, be received from one or more other devices, such as a measuring device or one or more other sensors. Second sensor may be the same sensor (e.g., same type of sensor, same actual sensor) as first sensor. Second sensor may be a different sensor (e.g., different type of sensor, different actual sensor) as first sensor. Second data may be the same data (e.g., same type of data, same actual data) as first data. Second data may be different data (e.g., different type of data, different actual data) as first data. The second data may be received at a processor.

The second sensor may be one or more sensors, as described herein. For example, the second sensor may be a sensor (or other device) configured to detect a location of the animal, to detect the motion (or stillness) of the animal, to detect an orientation of the animal, etc. The second sensor may be one or more of a variety of form factors, including, but not limited to, an accelerometer, a gyroscope, a magnetometer, weighing scales, weight transducers, force transducers, displacement transducers, pressure transducers, weight sensors, force sensors, displacement sensors, pressure sensors, load cells, photographic cameras, video cameras, camcorders, contact thermometers, non-contact thermometers, and a combination thereof. In addition, or alternatively, second sensor may be one or more of optical sensors, optical reflecting sensors, LED/photodiode pair optical sensors, LED/phototransistor pair optical sensors, laser diode/photodiode pair optical sensors, laser diode/phototransistor pair optical sensors, optocouplers, optical fiber coupled optical sensors, magnetic sensors, weight sensors, force sensors, displacement sensors, pressure sensors, various proximity sensors, such as inductive proximity sensors, magnetic proximity sensors, capacitive proximity sensors, and/or a combination thereof.

Second data may be motion, location, orientation, etc., data of an animal. The motion, location, orientation, etc., data of the animal may be provided via one or more sensors or devices. The second data may be a signature of an animal event of the animal, as described herein. For example, the signature of the animal may be a scratching, turning (e.g., in circles), a crouching, a sniffing, a defection posture, a urination posture, a peristaltic movement, and the like.

The second data may confirm an animal event, for example, the animal event determined via the first data. As an example, first data may be an accelerometer data which indicates that the animal is crouching. Second data may be used to provide a location of the animal. For example, second data may indicate that the animal is in the waste area when the animal is crouching. In this example, the location data of the second data may confirm that the animal is performing a urination or defecation. In other examples, the first data and/or the second may include motion data, orientation data, location data, etc., of the animal.

At 706, the occurrence of an animal event may be identified. The animal event may be based on the first data and/or the second data. The animal event may be a urinating, defecating, eating, drinking, and/or resting of the animal. For example, based on one or more of the animal's motion, location, orientation, etc., a signature of an animal event of the animal may be determined. As described herein, a signature of an animal event may be a scratching, turning (e.g., in circles), a crouching, a sniffing, a defection posture, a urination posture, a peristaltic movement, and the like. An animal event (e.g., an animal urinating, defecating, eating, drinking, and/or resting) may be determined based on one or more signatures of the animal. Unsuccessful urinations and/or successful urinations may be determined via a signature. Unsuccessful defecations and/or successful defecations may be determined via a signature. Signatures may be used to determine a non-event, such as an event proximate to the feeding, drinking, waste, and/or rest area that aren't related to eating, drinking, urinating, defecating, and/or resting, respectively. At 708, the animal event may be displayed. For example, the animal event may be displayed on a display of a portable electronic device.

The health condition (e.g., illness, injury, disease, etc.) of the animal may be determined, for example, based on the animal event. For example, a health condition of the animal may be based on the amount of times the animal eats, drinks, sleeps, urinates, defecates in a time period, the duration of the eating, sleeping, urination, defecation, etc. The time period may be an hour, a day, a week, a month, or the like. The health condition may be based on a number of times the animal event occurs (e.g., within a predefined time period), a duration of the animal event, or the like. For example, a healthy animal may be expected to drink, eat, sleep, urinate, and/or defecate a minimum and/or maximum amount of times during a time period. A mean and median of the above parameters may be defined for a healthy animal and/or for an unhealthy animal. If the animal performs a defined health parameter less than or more than an amount defined for a healthy animal, the animal may be identified as being unhealthy (e.g., a sick, injured, diseased, etc.).

Figure 8:
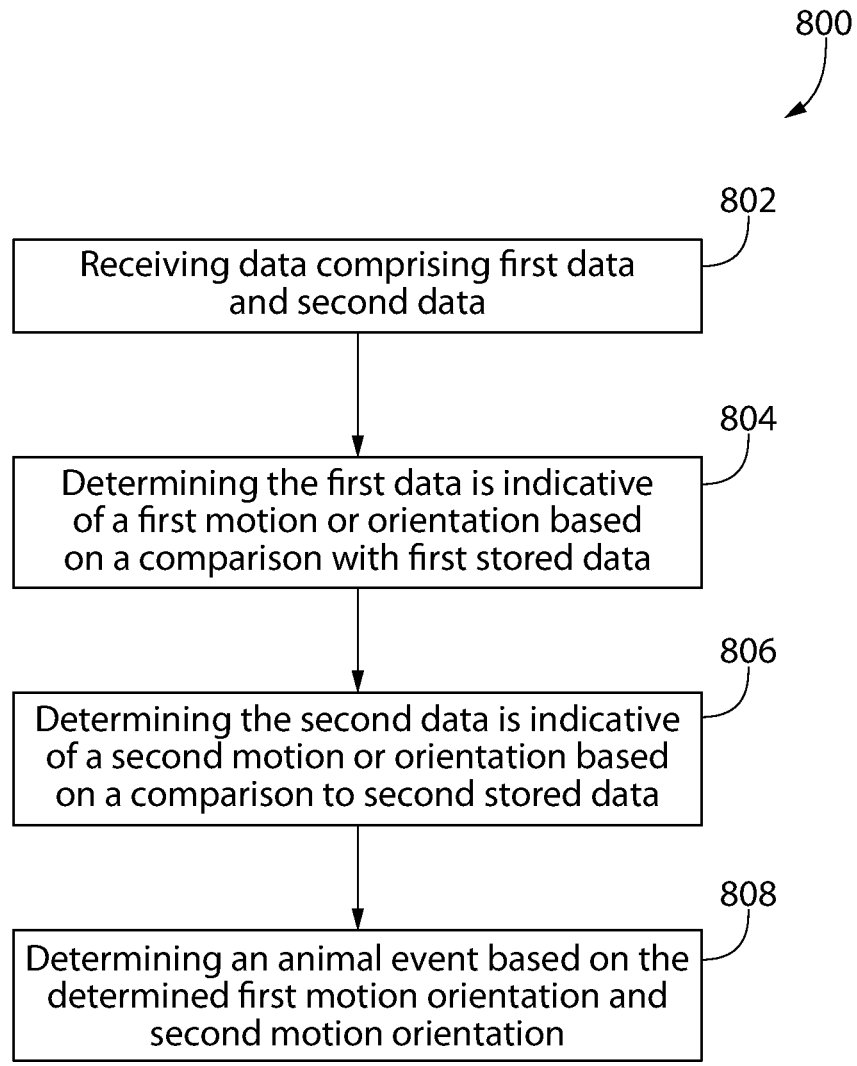
FIG. 8 is another example use of the system, as described herein.

FIG. 8 describes another example method of an animal monitoring. At 802, data may be received from one or more devices, such as one or more sensors, measuring devices, etc. For example, first data and/or second data may be received. The first data and/or the second data may be motion data, orientation data, location data, etc., as described herein.

At 804, first data may be compared with stored data. For example, stored data may be associated with an animal event, and first data may be compared with the stored data. The stored data may a signature of an animal event and/or data associated with a signature of an animal event. For example, the stored data may be data indicating that the animal is in a defecation posture. It may be confirmed (e.g., previously confirmed) that the stored data is a signature of an animal event, for example, via an eyewitness corresponding the data and the signature. First data may be compared with the stored (e.g., stored) first data to determine if the first data is indicative of a motion of the animal. For example, accelerometer data of the stored first data may be confirmed to be a digging of the animal. The first data may include accelerometer data of the animal. If the accelerometer data of the first data is equivalent (e.g., substantially equivalent) to the accelerometer data of the stored first data (in which the accelerometer data of the stored first data is confirmed to have been a digging), it may be determined that the first data is associated with a digging.

At 806, second data may be compared with stored data. For example, stored data may be associated with an animal event, and second data may be compared with the stored data. The stored data may a signature of an animal event and/or data associated with a signature of an animal event. For example, the stored data may be data indicating that the animal is in a defecation posture. It may be confirmed (e.g., previously confirmed) that the stored data is a signature of an animal event, for example, via an eyewitness corresponding the data and the signature. Second data may be compared with the stored (e.g., stored) second data to determine if the second data is indicative of a motion of the animal. For example, accelerometer data of the stored second data may be confirmed to be a digging of the animal. The second data may include accelerometer data of the animal. If the accelerometer data of the second data is equivalent (e.g., substantially equivalent) to the accelerometer data of the stored second data (in which the accelerometer data of the stored second data is confirmed to have been a digging), it may be determined that the second data is associated with a digging. Although motion (e.g., accelerometer) data is described in respect to first data and second data, it should be understood that first data may be any data representative of an animal (including, but not limited to, orientation data, location data, motion data, biometric data, etc.).

At 808, an animal event may be determined based on the first data and/or the second data. The first data and/or the second data may be a signature of an animal event. For example, a first data may be a signature of the animal digging. Second data may be a signature that the animal is in a urination posture. Based on first data indicating that the animal is digging and the second data indicating that the animal is in a urination posture, it may be determined that the animal is urinating. As described herein, the time of the signature and/or animal event, the duration of the signature and/or animal event, the location of the signature and/or animal event, the frequency of the signature and/or animal event, etc., may be determined.

A health condition (e.g., illness, injury, disease, etc.) of the animal may be determined, for example, based on the animal event. For example, a health condition of the animal may be based on the amount of times the animal eats, drinks, sleeps, rests, urinates, defecates in a time period, the duration of the eating, sleeping, urination, resting, defecation, the location of the eating, sleeping, urination, resting, defecation, etc. The time period may be an hour, a day, a week, a month, or the like. The health condition may be based on a number of times the animal event occurs (e.g., within a predefined time period), a duration of the animal event, or the like. For example, a healthy animal may be expected to drink, eat, sleep, urinate, and/or defecate a minimum and/or maximum amount of times during a time period. A mean and median of the above parameters may be defined for a healthy animal and/or for an unhealthy animal. If the animal performs a defined health parameter less than or more than an amount defined for a healthy animal, the animal may be identified as being unhealthy (e.g., a sick, injured, diseased, etc.).

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. A method comprising:
    fastening an activity collar to an animal and generating continuous first data from a first sensor device located upon a surface of the collar;
    providing one of a waste area, a feeding bowl, or a drinking bowl and generating continuous second data from a second sensor device;
    receiving, at a processor, the continuous first data from the first sensor device, the first data indicative of an animal event of the animal, the first sensor device being an accelerometer coupled to the animal, the animal event being detected by one of a change in acceleration, velocity, or position of the animal;
    receiving, at the processor, the continuous second data from the second sensor device that is separate and distinct from the first sensor device, the second data confirming an occurrence of the animal event, the second sensor device being a proximity sensor associated with one of the waste area, the feeding bowl, or the drinking bowl;
    identifying, at the processor, the occurrence of the animal event based on comparing the first data with stored first data and comparing the second data with stored second data;
    and causing the identified occurrence of the animal event to be displayed via a display device;
    where the display of the identified occurrence includes multiple data categories about the identified occurrence including a graph and an icon of the one or more of the waste area, the feeding bowl, or the drinking bowl based on the identified occurrence;

wherein the first data is indicative of a defecation posture of the animal and the second data is indicative of the animal being located within or about the waste area;

and wherein a defecation event is determined based on first data indicating the defecation posture of the animal is unchanged, a head of the animal is oriented in an upright orientation, a side to side movement of the animal, and a peristaltic movement of the animal.

2. The method of claim 1 further comprising determining, at the processor, a health condition of the animal based on the animal event.

3. The method of claim 2 wherein the determination of the health condition of the animal is based on a quantity of the animal event or a duration of the animal event.

4. The method of claim 1 wherein the animal event comprises at least one of a discharge event or a feeding event.

5. The method of claim 1 wherein the first data comprises accelerometer data indicative of a motion of the animal and the second data comprises magnetometer data indicative of an orientation of the animal.

6. The method of claim 1 wherein the proximity sensor comprises at least one of a scale, a motion detector, an RFID tag, an RFID reader, a GPS, a passive infrared, a microwave, or an ultrasound transducer.

* * * * *